(12) United States Patent
Hirschel et al.

(10) Patent No.: US 8,827,963 B2
(45) Date of Patent: Sep. 9, 2014

(54) ADMINISTERING DEVICE WITH HOLDING MECHANISM

(75) Inventors: Juerg Hirschel, Aarau (CH); Celine Kaenel-Jost, Zurich (CH); Ulrich Moser, Heimiswil (CH); Markus Tschirren, Kirchberg (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/853,713

(22) Filed: Aug. 10, 2010

(65) Prior Publication Data

US 2011/0130723 A1 Jun. 2, 2011

Related U.S. Application Data

(63) Continuation of application No. PCT/CH2009/000041, filed on Feb. 4, 2009.

(30) Foreign Application Priority Data

Feb. 11, 2008 (CH) ...................................... 0188/08

(51) Int. Cl.
*A61M 5/00* (2006.01)
*A61M 5/20* (2006.01)
*A61M 5/315* (2006.01)
*A61M 5/24* (2006.01)
*A61M 5/32* (2006.01)

(52) U.S. Cl.
CPC ....... *A61M 5/2033* (2013.01); *A61M 2205/583* (2013.01); *A61M 2205/582* (2013.01); *A61M 5/31511* (2013.01); *A61M 5/2448* (2013.01); *A61M 5/32* (2013.01); *A61M 2205/581* (2013.01)

USPC ............................................ 604/234; 604/110

(58) Field of Classification Search
CPC . A61M 5/2033; A61M 5/24; A61M 5/31511; A61M 5/315
USPC ........................ 604/110, 187, 197, 232–234
See application file for complete search history.

(56) References Cited

U.S. PATENT DOCUMENTS

| 2,752,918 | A | | 7/1956 | Uytenbogaar | |
|---|---|---|---|---|---|
| 2,960,087 | A | | 11/1960 | Uytenbogaar | |
| 5,300,030 | A | * | 4/1994 | Crossman et al. | 604/136 |
| 5,620,421 | A | * | 4/1997 | Schmitz | 604/135 |
| 2005/0261634 | A1 | * | 11/2005 | Karlsson | 604/197 |

FOREIGN PATENT DOCUMENTS

| DE | 10 2005 032 705 | 11/2006 |
|---|---|---|
| DE | 10 2005 038 933 | 2/2007 |
| WO | WO 2004/054644 | 7/2004 |
| WO | WO 2008/005315 | 1/2008 |

\* cited by examiner

*Primary Examiner* — Aarti B Berdichevsky
*Assistant Examiner* — Bradley Osinski
(74) *Attorney, Agent, or Firm* — Dorsey & Whitney LLP; Stuart R. Hemphill, Esq.

(57) ABSTRACT

An apparatus for administering a substance, e.g. a medicinal, pharmaceutical, or cosmetic substance, includes a driving member movably mounted within the apparatus to administer the substance, and the driving member includes a holding feature or components of a holding feature which holds or retains at least one additional element of the apparatus in a position relative to the apparatus. In some embodiments, the additional element is a carpule or ampoule containing the substance, and the holding feature retains the carpule or ampoule in a position within a carpule or ampoule holder.

10 Claims, 6 Drawing Sheets

ADMINISTERING DEVICE WITH HOLDING MECHANISM

CROSS-REFERENCED RELATED APPLICATIONS

This application is a continuation of International Patent Application No. PCT/CH2009/000041 filed Feb. 4, 2009, which claims priority to Swiss Patent Application No. 188/08 filed Feb. 11, 2008, the entire contents of each are incorporated herein by reference.

BACKGROUND

The present invention relates to devices for administering, injecting, infusing, delivering or dispensing a substance, and to methods of making and using such devices. More particularly, it relates to a device (which also may be thought of and/or referred to as an apparatus or appliance) for administering a fluid or liquid product or substance, such as a medicinal, pharmaceutical, cosmetic or other therapeutic substance or agent. More particularly, the present invention relates to an injection appliance for delivering a fluid product into body tissue.

Administering devices of the type to which the present invention relates generally comprise a large number of individual structural components or pieces at least some of which are movable relative to one another. In may cases, the individual components make up structural assemblies or operational units, some of which may also be relatively moveable and/or moveable relative to the device as a whole. An example is an administering mechanism for causing, carrying out or driving an administering operation. Typically, such administering devices include a container or receptacle for the substance to be administered.

With further reference to administering mechanisms, they may include a drive member moveable inside the administering device to expel the fluid product from the administering device. The receptacle for the fluid product can comprise several components, e.g. a vial, a glass carpule, an ampoule, a containing structure integrated with the device, etc., in which an active substance is received. In some instances, use may be made of a carpule or ampoule holder in which the carpule or ampoule is accommodated. In some administering devices, the receptacle can be uncoupled from the administering mechanism, for example to fit a new receptacle or a new carpule after an empty carpule has been removed and/or discarded. Disposable administering devices are also known, wherein after the receptacle is empty, the entire administering device, together with the administering mechanism and the receptacle, is discarded. Semi-disposable devices are also known.

For any administering device, to help ensure exact dosing when the product to be administered is expelled or delivered, it is necessary that at least some of the individual structural parts of the administering device are arranged in or moveable to a defined (or certain, specific or selected) position or defined positions relative to one another. If, for example, there is too much play between the individual structural parts, it is possible that, when the drive member is actuated or moved, it will not cover a defined distance, e.g., a dosing distance, necessary for expelling a quantity of fluid product corresponding to the desired dose. The dosing distance would be, in this case, imprecise, i.e., an excessive or deficient amount of product may be administered. In administering devices of the type relating to the present invention, it is therefore best to hold at least some of the individual structural parts in a defined position relative to one another.

DE 10 2005 032 705 A1 discloses an injection appliance that has a housing for receiving an administering mechanism and a carpule holder in which a carpule can be fitted. The carpule holder is attached to the housing. A drive member of the administering mechanism engages on a stopper in the carpule to advance the stopper in the carpule during an advancing movement of the drive member to expel the substance to be administered from the carpule by way of an attached injection needle. The housing of the injection appliance, or a part of the injection appliance fixed to the housing, has a plastic spring which is stationary relative to the housing. When the carpule holder is fitted into the housing, the plastic spring engages on the proximal end of the carpule and, by its pretensioning, presses the carpule against a shoulder arranged distally on the carpule holder. By the plastic spring fixed to the housing, the carpule is held in the carpule holder and does not move undesirably relative to the carpule holder. Because of the plastic spring, the overall length of the injection appliance is increased, and, during the manufacture of the injection appliance, an additional assembly step is needed to introduce the plastic spring.

SUMMARY

It is an object of the present invention to provide a device for administering a substance wherein at least some of the components of the device have and/or assume a defined position with respect to one another, the device having as few components as possible and being easy to assemble.

In one embodiment in accordance with the present invention, a device for administering a fluid product is provided, comprising a drive member which, for administering the fluid product, is movable in the administering device, the drive member comprising a holding mechanism or components of a holding mechanism, by which at least one further element of the administering device is held in a certain position.

In one embodiment, the present invention comprises an apparatus for administering a substance, e.g. a medicinal, pharmaceutical, or cosmetic substance, comprising a driving member movably mounted within the apparatus for administering the substance, the driving member comprising a holding feature or components of a holding feature which holds or retains at least one additional element of the apparatus in a position relative to the apparatus. In some embodiments, the additional element is a carpule or ampoule containing the substance, and the holding feature retains the carpule or ampoule in a position within a carpule or ampoule holder.

In some embodiments, the drive member can be a component or part of an administering mechanism and can, for example, take the shape or be thought of as a piston rod. In some embodiments, the piston rod can be, for example, toothed or threaded. The drive member can be actuated manually and/or be driven by a spring element, for example a coil spring or helical spring. It is, of course, also possible that the administering mechanism comprises a dosing device and a display device. In some embodiments, the drive member is movable relative to the administering device, e.g., along a longitudinal axis of the administering device and/or the housing thereof. A combined rotational and advancing or translational movement is also conceivable.

In accordance with some embodiments of the present invention, the drive member comprises a holding mechanism or feature, which holds at least one further element of the administering device. Such a further element can be, for example, a receptacle for receiving the fluid product or for receiving a container for the fluid product. In some embodiments, the further element may be part of or operably coupled with other elements of the administering device, e.g., the administering mechanism, a dosing mechanism or a display mechanism.

In some embodiments according to the present invention, the drive member may comprise only portions of a holding mechanism. In this case, at least one further holding element is provided. Thus, for example, the holding portions of the drive member can hold one element in a first direction, i.e. can block or prevent movements of the element relative to other components of the administering device in a first direction. The further holding element, associated with another component of the administering device, may block or prevent movement of the one element in a second direction of movement. The term holding is to be understood generally as a securing, preventing, locking or blocking of a movement of the element to be held relative to other components of the administering device. For example, a holding mechanism according to the present invention can hold a receptacle for the fluid product in a selected position relative to a housing of the administering device, or a carpule containing the fluid product is held inside a receptacle associated with the administering device.

In some preferred embodiments, the drive member and the holding mechanism are fixedly connected to each other, are integral or are formed as one piece.

The holding mechanism, according to some embodiments of the present invention, holds at least one further element or component of the administering device in a defined position in the administering device. The defined position is determined by the local arrangement of the element to be held relative to the other components of the administering device. It is therefore possible that the element to be held assumes a defined, secured position relative to a first component, while being able to assume different positions relative to a second component. For example, a carpule in a carpule holder of the administering device can be held in a defined position, while the carpule holder moves relative to the housing of the administering device.

In some preferred embodiments, the holding mechanism holds the element in the defined position in a starting position of the drive member and in an advanced position of the drive member in which the drive member is moved relative to the at least one further element in relation to the starting position. For example, a carpule is held in a carpule holder by the drive member, both in a starting position of the drive member and also in an advanced position in which the drive member is moved relative to the carpule and to the carpule holder.

In one preferred embodiment, the holding mechanism comprises holding arms protruding or extending from the drive member. In the starting position of the drive member, the holding arms protrude or extend laterally from a longitudinal axis of the drive member and can move flexibly. When the drive member is moved to the advanced position, the holding arms can advantageously be moved flexibly to be able to maintain their holding function. For example, they can be moved flexibly toward or away from the longitudinal axis.

In some embodiments, the holding by the holding mechanism can be effected by at least one axial abutment against which the at least one further element of the administering device abuts. Moreover, the holding can also be effected by a press fit with the at least one further element. In some preferred embodiments, in the starting position of the drive member, the holding mechanism holds the at least one further element by at least one axial abutment of the element on the holding mechanism or the holding arms, and in an advanced position of the drive member, the holding of the holding mechanism or of the holding arms is effected by a press fit with the further element of the administering device. It is also possible for a holding abutment to act in addition to the press fit.

In some embodiments, the drive member can hold the at least one further element by at least one first axial abutment in the starting position and by at least one second axial abutment in the advanced position. During the transition from the starting position to the advanced position, there is therefore a transition from the first holding abutment to the second holding abutment to hold the at least one further element.

In some preferred embodiments, the at least one abutment, e.g. the first axial abutment, has an oblique surface, which is inclined relative to the longitudinal axis in the distal direction. (In the context of the present application, the terms "distal" and/or "distal end" are intended to refer generally to the end of the administering device from which the fluid product emerges; the opposite end may be thought of and/or referred to as the proximal end.) The oblique surface allows the at least one element to slide down the abutment. In this way, for example, the transition can take place from the at least one axial abutment to the holding by a press fit or to a second axial abutment.

According to one illustrative embodiment of the present invention, the administering device comprises a housing, a holding mechanism and a receptacle for receiving a container for the fluid product, the receptacle being connected or connectable to the housing, and the holding mechanism holds the container in a defined position in the receptacle. The drive member is in the form of a piston rod which, at its distal end, has a holding mechanism in the form of two holding arms that are spreadable and/or spread out relative to the longitudinal axis. To administer a fluid product from the administering device, the drive member is moved relative to the housing and to the receptacle.

In the starting position of the drive member, the holding arms of the holding mechanism abut against a proximal end of the container. If the container is formed, for example, by a sleeve-like, cylindrical glass carpule, the holding arms can abut against the edge of the carpule, i.e., the distal end of the holding arms forms an axial abutment for the carpule. They have oblique surfaces which are inclined in the distal direction toward the longitudinal axis. If the drive member is now advanced relative to the receptacle, the holding arms of the holding mechanism slide down the edge of the carpule and abut against a stopper in the container. In doing so, the spread-open holding arms can move flexibly in the direction of the longitudinal axis of the drive member and inward into the container. At the same time, it is possible that the holding arms rest on the inside wall of the container and form a press fit. In this case, the flexible holding arms of the holding mechanism at the same time serve to hold the container in the receptacle and as an advancing ram for moving the stopper forward in the container to administer the fluid product. In principle, however, it is also possible to arrange the holding arms laterally on the drive member and set back in relation to the distal end of the drive member, such that they can rest laterally on the drive member in an advance position, in which case the advancing ram is formed by the front end of the drive member. In this embodiment, the holding mechanism of the drive member secures the container for the fluid product inside the receptacle against a movement in the proximal direction out of the receptacle.

In some embodiments, it is also possible to supplement the holding mechanism with further holding elements. For example, the receptacle can have a counter-abutment against which the container abuts in the distal direction. In this case, the container inside the receptacle is also secured against a movement in the distal direction.

According to another embodiment of the present invention, the holding mechanism of the drive member serves to hold the container while the receptacle is moved relative to the drive member and to the housing, with the drive member remaining stationary relative to the housing. Such a situation arises, for example, when using two-chamber carpules or ampoules in which a solvent is accommodated in a first chamber and a dry or lyophilized active substance is accommodated in a second chamber. The two chambers are delimited by two stoppers and the carpule wall. To mix the active substance with the solvent, the stoppers inside the carpule are moved in such a way that the stopper separating the chambers frees a bypass, such that the solvent is able to flow out of the one chamber into the active substance chamber. The stoppers can be advanced, for example by screwing or pushing the receptacle into the housing of the administering device. While the receptacle is being screwed or pushed in, the stoppers are moved inside the container by the resistance of the drive member. The drive member remains stationary relative to the housing.

An advantage of the present invention is that a separate holding part, e.g. a holding spring, is not needed for fixing and/or moving components of the administering device. In an administering device according to the present invention, the drive member of the administering mechanism assumes and/or provides the holding function. There is no requirement for additional structural parts which increase the volume of the administering device and/or make assembly more difficult. Moreover, the holding mechanism according to the present invention can perform its holding function even when the element to be held is moved relative to the holding mechanism or to the drive member.

DETAILED DESCRIPTION

Figure 1:
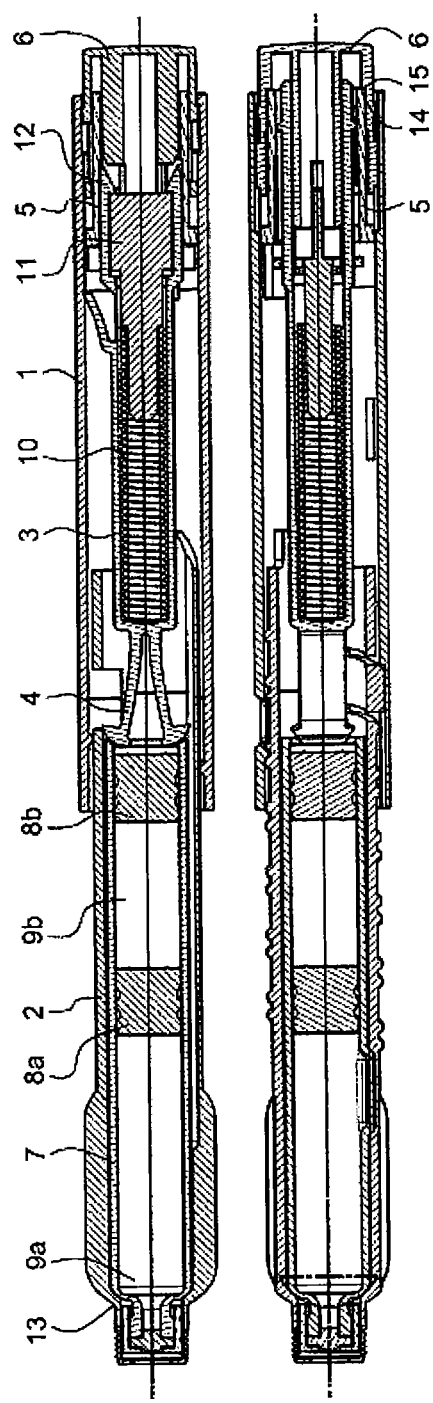
FIG. 1 shows an embodiment of an administering device in accordance with the present invention in a starting state.

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless otherwise indicated specifically or by context, positional terms (e.g., up, down, front, rear, distal, proximal, etc.) are descriptive not limiting. Same reference numbers are used to denote same parts or components.

FIGS. 1-5 show an embodiment of an administering device according to the present invention with a holding mechanism for holding an element of the administering device. FIGS. 6a and 6b show another embodiment of a holding mechanism for holding an element of the administering device. FIGS. 1 to 5, in each case, show two views, of which the second view, at the bottom, is turned through 90° in relation to the first view, at the top.

The administering device depicted in FIGS. 1-5 uses a two-chamber carpule (which also may be thought of and/or referred to as an ampoule) as container for a fluid product. The fluid product is discharged or delivered from the carpule by a drive member being moved forward by a discharging spring. The product is therefore discharged automatically as soon as the discharging spring is activated. The administering device has a fixed dose, i.e. the discharge volume is fixed. The forward movement of the drive member is therefore also fixed and cannot be adjusted. The administering device is blocked or locked after a single discharge procedure and is discarded after the discharge procedure. However, it should be clear to a person skilled in the art that a holding mechanism according to the present invention can be used equally advantageously in reusable administering devices, in devices with individual dosing or manual discharge, and also in devices with single-chamber carpules.

With reference to FIG. 1-5, the administering device has a housing 1, a receptacle for receiving the fluid product in the form of a carpule holder 2, a drive member 3 with a holding mechanism in the form of holding arms 4, a blocking mechanism in the form of a blocking ring 5, and an actuation element in the form of a trigger button 6.

A two-chamber carpule 7 is accommodated in the carpule holder 2. The two-chamber carpule has a first stopper 8a and a second stopper 8b. The second stopper 8b closes the two-chamber carpule at the proximal end. At the distal end, the two-chamber carpule has a narrowed area whose opening is closed off by a membrane. The membrane can be pierced by a needle, e.g. of a suitable injection needle unit. The injection needle unit is not shown in the figures. A first chamber 9a, in which a dry or lyophilized active substance is accommodated (not shown), is formed between the membrane and the first stopper 8a. A second chamber, in which the solvent for the active substance is stored, is formed between the first stopper 8a and the second stopper 8b.

The drive member 3 has a sleeve-shaped configuration. A drive spring 10, arranged in the inside of the drive member 3, is clamped between a distal abutment at the sleeve base of the drive member and a proximal abutment on an element 11 fixed to the housing. In the starting state, shown in FIG. 1, the drive member 3 is held relative to the housing element 11 by snap-action arms 12, which releasably snap or move in behind an abutment of the housing element 11. At the distal end of the drive member 3, the holding arms 4 are mounted in such a way that they protrude or extend laterally from a longitudinal axis of the drive member in the starting position. In the embodiment depicted, two holding arms 4 are shown spread apart from each other. It is of course also possible to provide three or more such holding arms. In the starting state depicted in FIG. 1, the holding arms 4 abut with their distal ends against a proximal (rear or rearward) edge of the carpule 7. The holding arms 4 press the carpule 7 against a shoulder 13 of the carpule holder 2. The carpule 7 is therefore held in a defined position, relative to the carpule holder 2, by the holding mechanism in the from of the holding arms 4. This prevents the carpule from moving back and forth in the proximal (rearward) and distal (forward) directions in the holder.

In the starting state shown in FIG. 1, the blocking ring 5 is located in a blocking position in which it blocks or prevents an actuation of the trigger button 6, i.e. the trigger button 6 cannot be pressed in the longitudinal direction into the housing 1. For this purpose, the blocking ring 5 has a blocking abutment 14, which rests on a counter-abutment 15 on the trigger button 6. By the blocking abutment 14 of the blocking ring 5 and the counter-abutment 15 of the trigger button 6 abutting each other, the trigger button 6 cannot be actuated, that is to say it cannot be pressed into the housing along the longitudinal axis of the housing. For this purpose, the blocking ring 5 is mounted fixedly relative to the housing in the longitudinal direction but can be rotated relative to the housing. The blocking abutment 14 can be formed, for example, by ribs or cams on the blocking ring or by the proximal edge of the blocking ring 5.

The blocking ring 5 is generally cylindrical, having a sleeve-shaped configuration, and surrounds the snap-action arms 12 of the drive member 3. In the starting state shown in FIG. 1, the inner circumferential surface of the blocking ring 5 bears on the outside of the snap-action arms 12 in such a way that the arms cannot be released from their snap-in engagement behind the housing element 11. The blocking ring 5 thus blocks an actuation of the trigger button 6 and also a release of the snap-action arms 12. The starting state corresponds to the purchase or delivery state in which the administering device is supplied to a user. An actuation of the administering device is not possible in this state.

Figure 2:
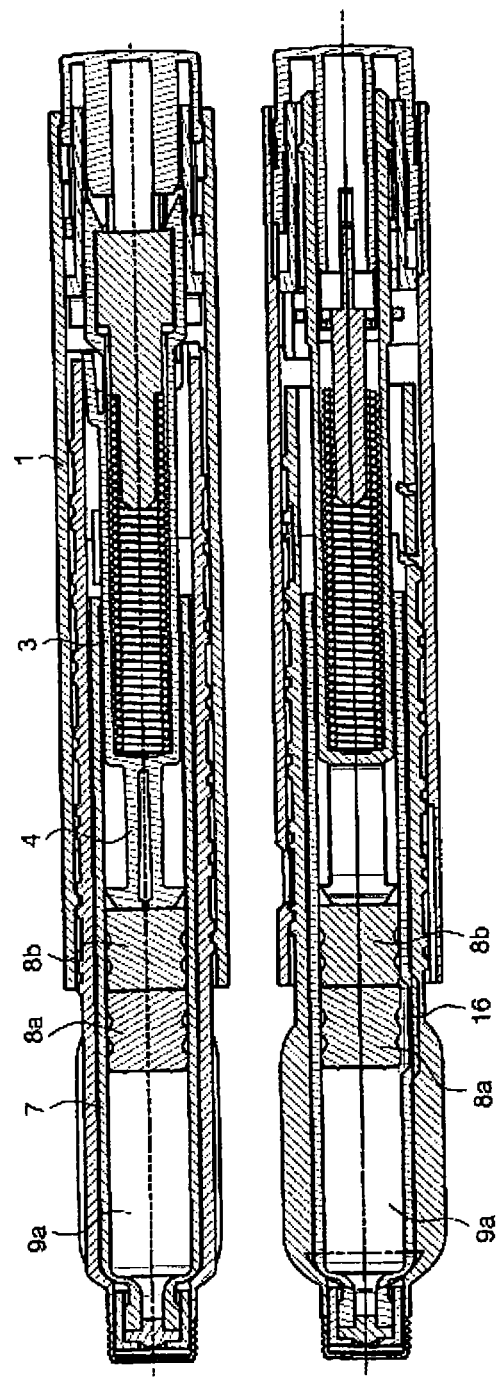
FIG. 2 shows the administering device in a state when mixing has taken place.

FIG. 2 shows the administering device in a state when mixing has taken place, in which state the active substance of the chamber 9a of the two-chamber carpule 7 has been mixed with the solvent of the chamber 9b. In some embodiments, the completion of the mixing procedure can be indicated by a tactile, acoustic and/or visual signal. As is shown in FIG. 2, mixing was achieved by moving the stoppers 8a and 8b inside the carpule 7 until the stopper 8a comes to lie on a bypass 16 through which the solvent can flow into the chamber 9a and the stopper 8b comes to lie on the stopper 8a. For advancing the stoppers, the carpule holder 2 is screwed into the housing 1 such that the drive member, which in this state is at rest relative to the housing, moves the stoppers 8a and 8b relative to the carpule 7. To screw the carpule holder in, an inner thread is provided on the inside of the housing and an outer thread is provided on the outside of the carpule holder.

As can be seen in FIG. 2, the holding arms 4 have slipped from the proximal edge of the carpule 7 and have been moved radially inwardly in the direction of the longitudinal axis of the drive member. For this purpose, the ends of the holding arms 4 have oblique surfaces along which the holding arms 4 are deflected inwardly as soon as the proximal edge of the carpule 7 is pressed with sufficient force against the oblique surfaces, as is the case when the carpule holder 2 is screwed into the housing 1. The holding arms 4 move in toward each other and form a ram for the stopper 8b of the carpule 7. Via the holding arms 4 abutting against the stopper 8b, the carpule 7 is further held in its defined position in the carpule holder 2, while the stoppers 8a and 8b are moved inside the carpule 7. Independently of this, the holding arms 4 form a press fit with the inside wall of the carpule 7, i.e. they have radially outward pretensioning since having been bent radially inwardly. The press fit serves to hold the carpule in a defined position in the carpule holder. The holding mechanism according to the present invention, or part of the holding mechanism, of the drive member can therefore assume two functions, holding the carpule and stopping the advancing movement of the drive member.

After the mixing procedure of the two-chamber carpule, it may be necessary for the chamber 9a, with the dissolved active substance, to have air removed from it before the active substance can be injected. For this purpose, an injection needle unit is mounted on the distal end of the carpule holder 2, in such a way that a needle pierces the membrane of the carpule 7 and, thus, creates a fluid connection to the chamber 9a. Screwing in the carpule holder 2 slightly further leads to a further advancing movement of the stoppers 8a and 8b, such that air located in the chamber 9a can escape. The advancing movement is normally carried out until a small amount of the active substance 9a emerges from the needle of the injection needle unit. The completion of the air removal procedure can be indicated by a tactile, acoustic and/or visual signal.

Figure 3:
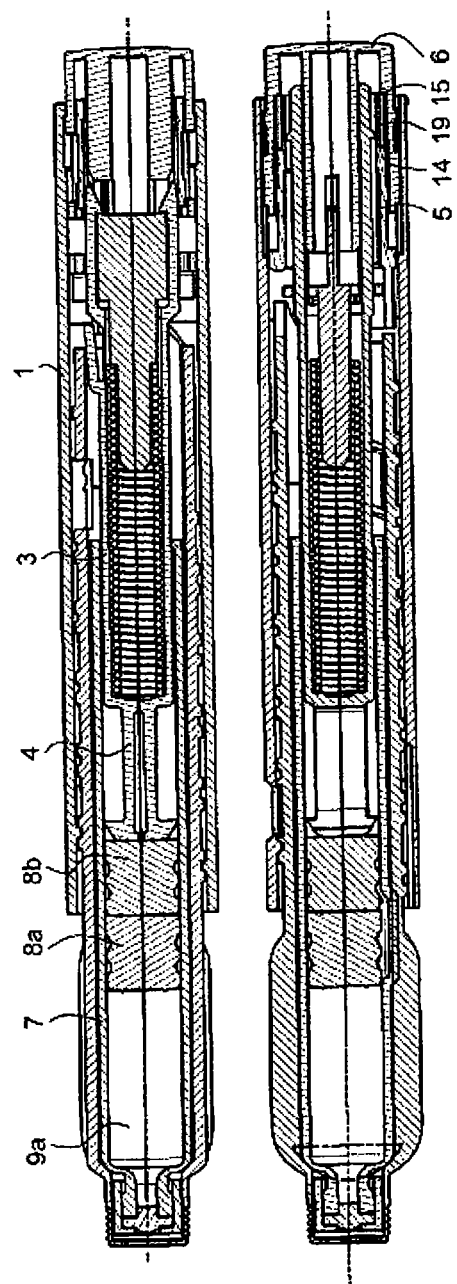
FIG. 3 shows the administering device in a state when air has been removed.

The operational state with the air removed is shown in FIG. 3. The injection needle unit is not shown. In the last screwing-in movement of the carpule holder 2 into the housing 1, in which air can also be removed from the carpule, the blocking ring 5 is moved from the blocking position to a release position. As is shown in FIGS. 6a-6d, the carpule holder for this purpose has an abutment 17, and the blocking ring has a counter-abutment 18. The abutment 17 of the carpule holder 2 is designed such that it abuts in the circumferential direction against the counter-abutment 18 of the blocking ring 5 during the rotation movement of the carpule holder. Upon further rotation of the carpule holder 2, the carpule holder carries the blocking ring 5 along with it, such that the blocking ring 5 is rotated relative to the housing 1 and to the trigger button 6. By this rotational movement, the blocking ring is moved from the blocking or locked position to the release position. As is shown in FIG. 3, during the rotation the blocking abutment 14 of the blocking ring 5 is rotated away from the counter-abutment 15 of the trigger button 6 until the counter-abutment 15 lies opposite a groove or channel 19 of the blocking ring, inside which groove or channel 19 the counter-abutment 15 of the trigger button 6 can be moved in the longitudinal direction.

During the rotation of the blocking ring 5 by the carpule holder 2, the inner surfaces of the blocking ring 5, which prevent the snap-action arms 12 from disengaging from their snap-in position, are also rotated away from this position. In the release position of the blocking ring 5, the snap-action arms 12 lie opposite recesses in the sleeve face of the blocking ring 5. The blocking ring 5 is therefore also located in a release position with respect to the snap-action arms 12.

Figure 4:
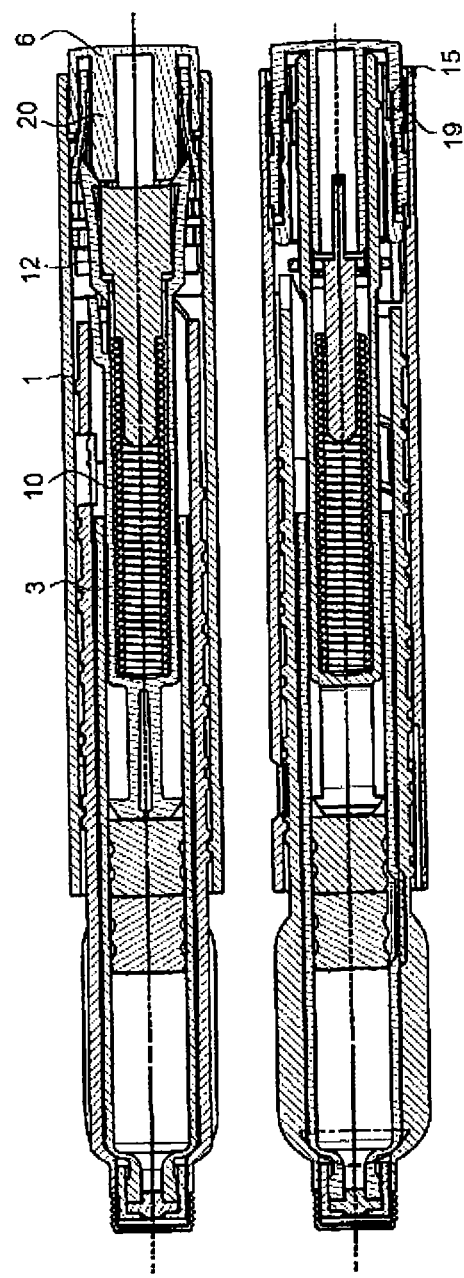
FIG. 4 shows the administering device in a triggered state.

FIG. 4 shows the administering device in a triggered state in which the trigger button 6 has been pressed into the housing 1 along the longitudinal axis of the housing 1. The counter-abutments 15 of the trigger button 6 have been moved inside the channels 19 of the blocking ring 5. The trigger button 6 has inwardly extending webs 20 which, when the trigger button is in the triggered or pushed-in state, bear against oblique surfaces on the proximal end of the snap-action arms 12 and spread the arms 12 radially outwardly as the trigger button 6 moves forward, such that the ends of the snap-action arms come to lie inside the recesses in the blocking ring 5. The securing of the drive member 3 on the housing element 11 is canceled or ended by the spreading-open of the snap-action arms 12. In the triggered state, the spring force of the drive spring 10 begins to act and presses against the drive member 3.

Figure 5:
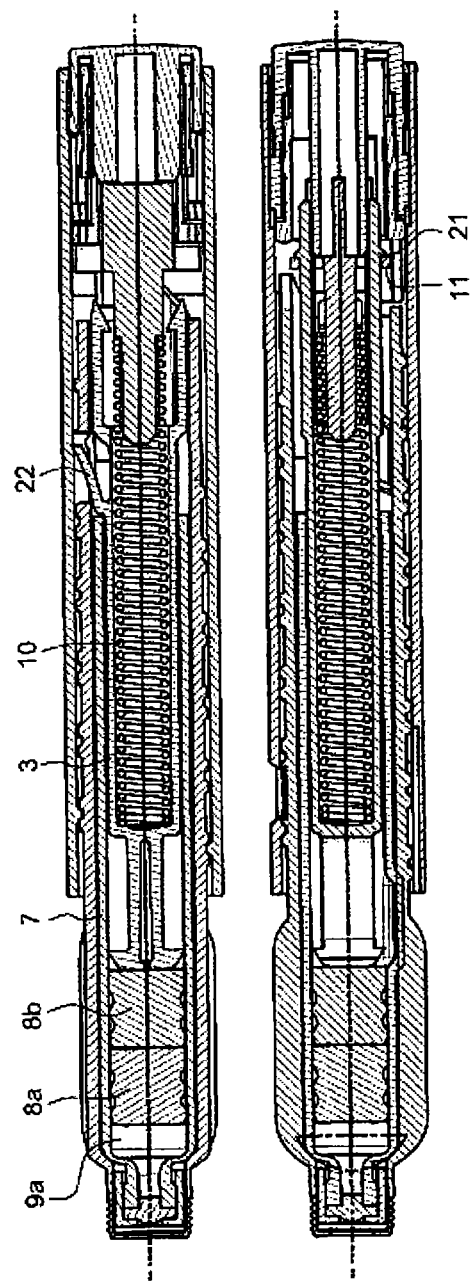
FIG. 5 shows the administering device after a product has been discharged or administered.
Figure 6A:
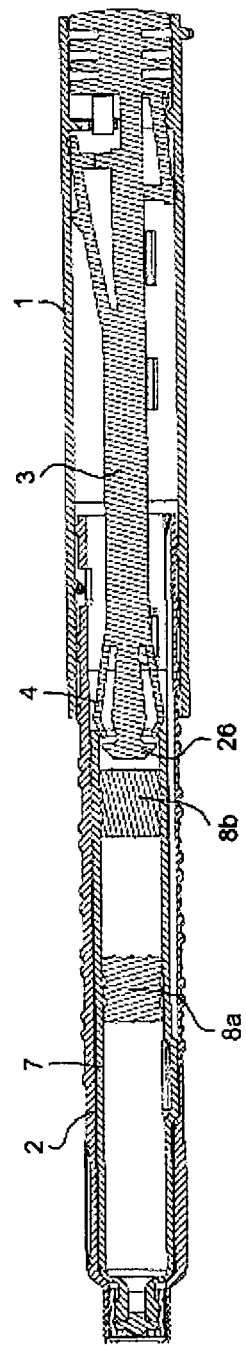
FIG. 6a is a sectional drawing of another embodiment of an administering device in accordance with the present invention with a holding mechanism in a starting position.
Figure 6B:
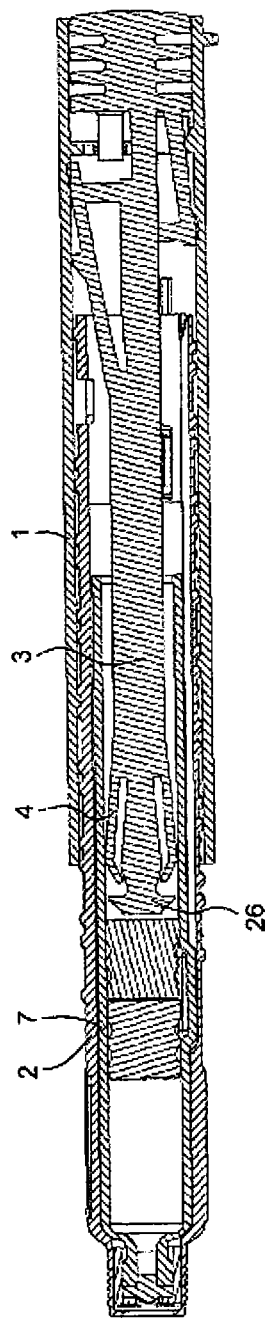
FIG. 6b is a detailed view of the embodiment of FIG. 6a in an advanced position.

As is shown in FIG. 5, the drive member 3 is moved forward relative to the carpule 7 by the force of the spring 10 and drives the stoppers 8a and 8b inside the carpule 7, such that the active substance is discharged from the chamber 9a. The drive spring 10 pushes the drive member 3 forward into the carpule until a projection 21, provided on the drive member 3, abuts against an edge of the housing element 11. As soon as the projection 21 abuts against the housing element 11, the discharging of the active substance is ended.

In the illustrative embodiment shown, a flexible arm 22, provided on the drive member 3, protrudes into a recess in the carpule holder, when the discharging has ended, and serves to block or prevent a movement of the drive member 3 in the proximal direction. Moreover, when it catches in the recess of the carpule holder, the arm 22 produces an acoustic noise, which indicates that the discharging has been completed.

FIGS. 6a and 6b show another embodiment of an administering appliance according to the present invention with a holding mechanism according to the present invention. In this embodiment, the drive member is driven by manual pressure. The holding mechanism of the drive member 3' has holding arms 4' which are arranged laterally on the drive member 3'. The distal (forward) end of the arms is set back in the proximal (rearward) direction relative to the distal (forward) end of the drive member 3'. As in the previously described illustrative embodiment, the holding arms 4' abut against the proximal edge of the carpule 7 fitted in the carpule holder 2. For this purpose, the holding arms 4' have oblique surfaces which bear on the edge of the carpule, as can be seen in FIG. 6a. The end of the holding arms 4' points inwardly into the carpule 7. As soon as the carpule holder 7 is inserted into the housing 1, the oblique surfaces of the holding arms 4' slide down the edge of the carpule, such that the holding arms 4' bend radially in the direction of the longitudinal axis of the drive member, as can be seen in FIG. 6b. In this embodiment, the holding arms 4' come to rest behind a ram 26, which is arranged on the front end of the drive member 3'. The ram 26 pushes against the stoppers 8a and 8b as soon as the carpule holder 2 is inserted into the housing 1. By inserting or screwing the carpule holder further into the housing, the stoppers are advanced inside the carpule 7 by the ram 26, in the same way as in the previously described illustrative embodiment.

In both the described exemplary embodiments, the carpule is held in the carpule holder initially by the abutment of the holding arms 4' against the edge of the carpule and then by a press fit between the pretensioned holding arms 4' and the inside wall of the carpule 7. In this way, the carpule 7 is held in a defined position at all times during use of the administering device.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

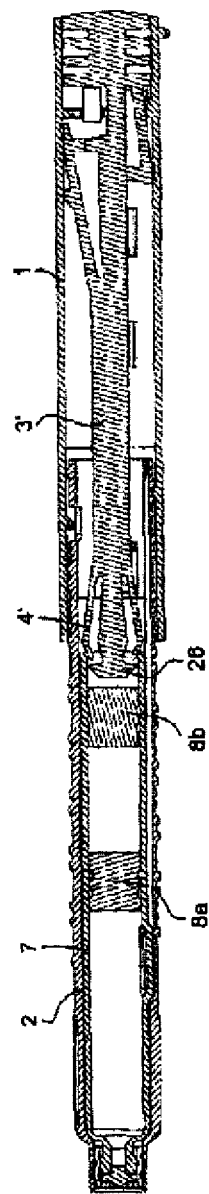
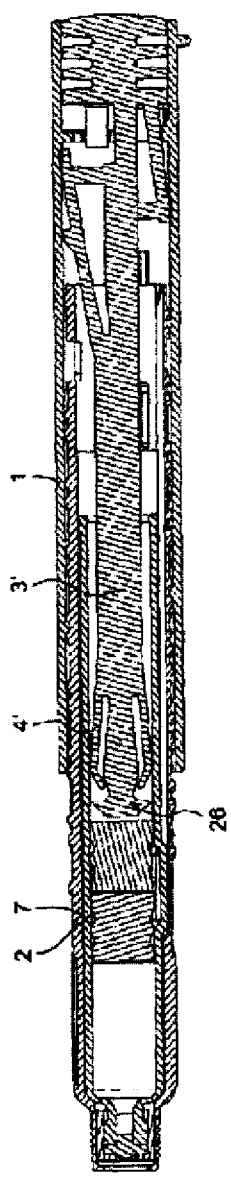

The invention claimed is:

1. A device for administering a fluid product, comprising a drive member movable in the administering device for administering the fluid product, the drive member comprising a holding mechanism by which a receptacle for receiving the fluid product is held in a defined position in the administering device, wherein the holding mechanism, in a starting position of the drive member and in an advanced position of the drive member in which the drive member is moved relative to the receptacle, holds the receptacle in the defined position, and wherein the holding mechanism comprises a flexibly movable holding arm protruding from the drive member, which holding arm in the starting position axially abuts the receptacle thereby holding it in the defined position and in the advanced position engages radially in a press fit with sidewalls of the receptacle thereby holding the receptacle in the defined position.

2. The device for administering a fluid product as claimed in claim 1, wherein the drive member and the holding mechanism are one piece.

3. The device for administering a fluid product as claimed in claim 1, wherein the holding mechanism, in the starting position, has at least one axial abutment for the receptacle.

4. The device for administering a fluid product as claimed in claim 3, wherein the at least one axial abutment has an oblique surface inclined relative to the longitudinal axis in the distal direction.

5. The device for administering a fluid product as claimed in claim 3, wherein the holding arm forms the axial abutment for the receptacle.

6. The device for administering a fluid product as claimed in claim 1, wherein the holding arm, in the starting position, protrudes laterally from a longitudinal axis of the drive member.

7. The device for administering a fluid product as claimed in claim 1, wherein the holding mechanism, in the starting position of the drive member, engages on a proximal end of the receptacle.

8. The device for administering a fluid product as claimed in claim 1, wherein the holding mechanism, in the advanced position of the drive member, abuts against a stopper in the receptacle.

9. The device for administering a fluid product as claimed in claim 8, wherein the holding mechanism forms a ram for moving the stopper.

10. The device for administering a fluid product as claimed in claim 1, wherein in the advanced position the holding arm flexibly engages radially in a press fit with sidewalls of the receptacle inside the receptacle.

* * * * *

UNITED STATES PATENT AND TRADEMARK OFFICE
CERTIFICATE OF CORRECTION

| | | |
|---|---|---|
| PATENT NO. | : 8,827,963 B2 | Page 1 of 2 |
| APPLICATION NO. | : 12/853713 | |
| DATED | : September 9, 2014 | |
| INVENTOR(S) | : Hirschel et al. | |

It is certified that error appears in the above-identified patent and that said Letters Patent is hereby corrected as shown below:

In the Drawings

Delete Drawing Sheet 6 of 6 and substitute therefore with the attached Drawing Sheet 6 of 6 consisting of corrected FIGS. 6a and 6b.

In the Claims

| Column | Line | Claim | Line | USPTO | Should Read |
|---|---|---|---|---|---|
| 10 | 44 | 8 | 2 | "in claim 1, wherein" | --in claim 7, wherein-- |

Signed and Sealed this
Twenty-fourth Day of March, 2015

Michelle K. Lee
*Director of the United States Patent and Trademark Office*